(12) United States Patent
Andersson et al.

(10) Patent No.: US 8,795,980 B2
(45) Date of Patent: Aug. 5, 2014

(54) METHODS FOR DETERMINATION OF PREVIOUS ETHANOL CONSUMPTION

(75) Inventors: Anders Andersson, Lund (SE); Anders Isaksson, Lund (SE)

(73) Assignee: Pethmark AB, Huddinge (SE)

( * ) Notice: Subject to any disclaimer, the term of this patent is extended or adjusted under 35 U.S.C. 154(b) by 0 days.

(21) Appl. No.: 13/809,356

(22) PCT Filed: Jul. 8, 2011

(86) PCT No.: PCT/SE2011/050925
§ 371 (c)(1),
(2), (4) Date: Mar. 28, 2013

(87) PCT Pub. No.: WO2012/005680
PCT Pub. Date: Jan. 12, 2012

(65) Prior Publication Data
US 2013/0224778 A1    Aug. 29, 2013

Related U.S. Application Data

(60) Provisional application No. 61/362,840, filed on Jul. 9, 2010.

(30) Foreign Application Priority Data

Oct. 12, 2010    (SE) ...................................... 1051068

(51) Int. Cl.
*C12Q 1/44*    (2006.01)
*G01N 33/98*    (2006.01)

(52) U.S. Cl.
USPC .......................................................... 435/19

(58) Field of Classification Search
USPC .................................................... 435/18, 19
IPC .................................... C12Q 1/44; G01N 33/98
See application file for complete search history.

(56) References Cited

U.S. PATENT DOCUMENTS

2006/0084134 A1 * 4/2006 Wurst .............................. 435/25

FOREIGN PATENT DOCUMENTS

WO    WO-2009/054784 A1    4/2009

OTHER PUBLICATIONS

Gupta R. et al. Lipase Assays for Conventional and Molecular Screening. Biotechnology Applied Biochemistry 37(Pt. 1)63-71, 2003.*

Tolonen, A. et al. "A method for determination of phosphatidylethanol from high density lipoproteins by reversed-phase HPLC with TOF-MS detection" *Analytical Biochemistry*, Jun. 1, 2005, 341(1):83-88.

Gnann, H. et al. "Identification of 48 homologues of phosphatidylethanol in blood by LC-ESI-MS/MS" *Analytical and Bioanalytical Chemistry*, Apr. 2010, 396:2415-2423.

Helander, A. et al. "Molecular Species of the Alcohol Biomarker Phosphatidylethanol in Human Blood Measured by LC-MS" *Clinical Chemistry*, Jul. 2009, 55(7):1395-1405.

Reichel, M. et al. "Increased Acid Sphingomyelinase Activity in Peripheral Blood Cells of Acutely Intoxicated Patients With Alcohol Dependence" *Alcoholism: Clinical and Experimental Research*, Jan. 2010, 34(1):46-50.

Hartmann, S. et al. "Phosphatidylethanol as a sensitive and specific biomarker—comparison with gamma-glutamyl transpeptidase, mean corpuscular volume and carbohydrate-deficient transferrin" *Addiction Biology*, Mar. 2007, 12(1):81-84.

Skeaff, C.M. et al. "Dietary-Induced Changes in Fatty Acid Composition of Human Plasma, Platelet, and Erythrocyte Lipids Follow a Similar Time Course" *The Journal of Nutrition*, Mar. 2006, 136(3):565-569.

International Search Report in International Application No. PCT/SE2011/050925, filed Jul. 8, 2011.

Ortiz, A. et al. "Interaction of diacyglycerols with phosphatidylcholine vesicles as studied by differential scanning calorimetry and fluorescence probe depolarization" *Biochemistry*, Dec. 1, 2988, 27(25): 9030-9036.

European Search Report dated Feb. 13, 2014 in European Application No. 11803909.8.

* cited by examiner

*Primary Examiner* — Ralph Gitomer
(74) *Attorney, Agent, or Firm* — Saliwanchik, Lloyd & Eisenschenk

(57) ABSTRACT

An improved method for assessing previous ethanol exposure comprises the steps of obtaining a sample from the body of a subject; quantitatively determining the level of one or several bio-precursors of phosphatidylethanol (PEth) (Formula I) or ethyl-sphingomyelin and the level of the corresponding one or several PEth (Formula II) or ethyl-sphingomyelin homologues in the sample; and obtaining a ratio between the level of one or several bio-precursors of PEth or ethyl-sphingomylein and the level of the corresponding one or several PEth- or ethyl-sphingomylein homologues. The ratio is indicative of previous ethanol consumption of the subject. Furthermore, a method for assessing previous absolute ethanol consumption can be accomplished by correlating the ratios of PEth precursor and PEth homologue levels in subjects to ratios obtained from reference subjects with known previous ethanol consumption.

22 Claims, 7 Drawing Sheets

PEth 16:0/18:1
(oleic acid)

PEth 16:0/18:2
(linoleic acid)

METHODS FOR DETERMINATION OF PREVIOUS ETHANOL CONSUMPTION

CROSS-REFERENCE TO RELATED APPLICATIONS

This application is the U.S. national stage application of International Patent Application No. PCT/SE2011/050925, filed Jul. 8, 2011, which claims priority to Swedish Application No. 1051068-3, filed Oct. 12, 2010, and U.S. Provisional Application No. 61/362,840, filed Jul. 9, 2010, the disclosures of each of which are incorporated herein by reference in their entirety.

TECHNICAL FIELD

The present invention relates to methods for detecting previous ethanol consumption. More specifically, the present invention relates to determination of ethanol bio-markers and the corresponding bio-precursors in a sample.

BACKGROUND

It is well known that a prolonged and high alcohol intake can lead to serious alcohol-related diseases and alcoholism. A low to moderate intake is, however, nowadays commonly accepted as beneficial due to the associated reduced risk of coronary heart disease. In order to assess a persons drinking behavior, e.g. for classifying this drinking behavior as healthy or unhealthy, relatively slowly eliminating direct bio-markers of ethanol is highly useful. One such bio-marker that has gained considerable interest over the last years is phosphatidylethanol (PEth).

PEth is an abnormal metabolite, formed by ethanolysis of precursor phospholipids with a glycerol backbone under catalytic influence of phospholipase D in the presence of ethanol. PEth exists in the form of several similar homologues, each with a unique set of long chain carboxylic acid residues as substituents. These homologues are commonly named in the form "PEth AA:B/CC:D", wherein AA indicates the number of carbons in the carboxylic acid substituent at the first position of the glycerol backbone and B indicates the number of double bonds encompassed by that carbon chain; CC indicates the number of carbons in the carboxylic acid substituent at the second position of the glycerol backbone and D indicates the number of double-bonds encompassed by that carbon chain. This nomenclature, however, does not indicate the position, nor the stereochemistry, of any present double-bonds. For example, the regio- and stereo-isomers (Z)-1-(palmitoyloxy)-3-([ethoxy(hydroxy)phosphoryl]oxy)prop-2-yl octadec-12-enoate and (E)-1-(palmitoyloxy)-3-([ethoxy(hydroxy)phosphoryl]oxy)prop-2-yl octadec-9-enoate are both named "PEth 16:0/18:1".

Clinically used analytical methods for the detection of PEth in blood-samples include HPLC-methods with evaporative light scattering (ELS) detection. A sum of different PEth-homologues are typically detected and used as a basis for quantification of PEth-levels.

Other analytical methods include methods which employ MS-detection of one or several selected homologues of PEth (see for example A. Tolonen et al, Analytical Biochemistry 2005, 341, 83-88). Sample throughput is usually greater in these analytical methods in comparison to methods which employ ELS-detection or similar techniques. Another advantage of methods with MS-detection is a lower detection limit of PEth in a sample, which allows for determination of a lower amount of previously consumed ethanol in a test subject. The MS-detector is typically tuned to discriminate between compounds based on their molecular weight in order to detect one or a few of the relatively more commonly occurring PEth-homologues.

Commonly occurring PEth-homologues in human blood after ethanol intake include 16:0/18:1 and 16:0/18:2.

WO2009054784A1 describes a method for assessing previous ethanol intake by measurement of PEth-homologues comprising mainly 16:0-, 18:0-, 18:1-, 18:2- or 20:4-carboxylic acid substituents, by employment of capillary electrophoresis and e.g. UV-detection.

Disadvantages of above mentioned methods for the determination of previous ethanol intake by the quantification of one or several PEth-homologues, include a high risk for erroneous conclusions regarding e.g. the amount of previously consumed ethanol due to the natural variability in PEth-homologue composition.

In addition, all of the above mentioned methods rely on simultaneous detection of several different PEth-homologues, or on the detection of one or a few selected PEth-homologues under the assumption that this selection gives a correct view of previous ethanol intake.

Hence, improved methods for the determination of previous ethanol intake are desired.

SUMMARY

It is an object of the present invention, considering the disadvantages mentioned above, to provide a method with a lowered risk for erroneous conclusions regarding the determination of previous ethanol intake, i.e. a method with a lower risk for false positives and/or false negatives.

It is another object of the present invention, to provide a simplified method for the quantification of PEth-homologues.

These and other objects, which will appear from the following description, have now been achieved by a method comprising the steps of: (i) obtaining a sample from the body of a subject; (ii) quantitatively determining the level of one or several bio-precursors of PEth and the level of the corresponding one or several PEth-homologues in the sample; and (iii) obtaining a ratio between the level of one or several bio-precursors of PEth and the level of the corresponding one or several PEth-homologues; wherein the subject is a human or animal.

According to another aspect, a method is provided comprising the steps of (i) obtaining a sample from the body of a subject; (ii) quantitatively determining the level of one or several bio-precursors of ethyl-sphingomyelin and the level of the corresponding one or several ethyl-sphingomyelin homologues in the sample; and (iii) obtaining a ratio between the level of one or several bio-precursors of ethyl-sphingomyelin and said level of the corresponding one or several ethyl-sphingomyelin homologues; wherein the subject is a human or animal.

According to yet another aspect, a method is provided comprising the steps of: (i) obtaining a blood sample of a subject; (ii) quantitatively determining the level of one or several PEth-homologues, or the level of one or several ethyl-sphingomyelin homologues, in the blood sample and determining the level of a measurable parameter representing an amount of cellular material in the blood sample; and (iii) obtaining a ratio between the level of one or several PEth-homologues or one or several ethyl-sphingomyelin homologues, and the level of the measurable parameter; wherein the subject is a human being or animal.

According to yet another aspect, a method is provided comprising the steps of: (i) obtaining a sample from the body of a subject; (ii) quantitatively determining the level of one or several bio-precursors of PEth, or one or several bio-precursors of ethyl-sphingomyelin, and the level of the corresponding one or several first bio-markers of ethanol being PEth or one or several ethyl-spingomyelin homologues, respectively, and quantitatively determine the level of a second bio-marker of ethanol; and (iii) comparing the levels of the one or several bio-precursors of PEth or one or several bio-precursors of ethyl-sphingomyelin, the level of the corresponding one or several first bio-markers of ethanol, and the level of the second bio-marker of ethanol; wherein the subject is a human or animal.

According to yet another aspect, a method is provided comprising the steps of: (i) obtaining a sample from the body of a subject; (ii) removal of the carboxylic acid residues from compounds of Formula II, i.e. PEth-homologues, present in the sample to yield a compound of Formula IIb by selective hydrolysis

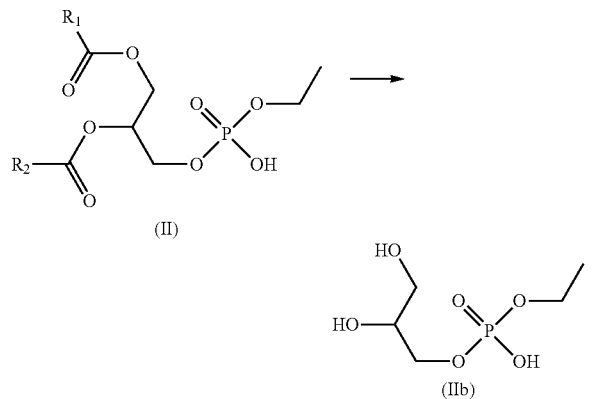

and (iii) quantification of the compound of Formula IIb; wherein the subject is a human or animal; and $R_1$ and $R_2$ are independently selected from straight or branched $C_{9-39}$ alkyl, $C_{9-39}$ alkenyl, $C_{9-39}$ alkdienyl and $C_{9-39}$ alktrienyl.

According to another embodiment, the method may comprise the steps of: removal of the carboxylic acid residues covalently bound as esters in one or several bio-precursors of PEth by selective hydrolysis to yield the corresponding alcohol or alcohols; quantitatively determining the level of the alcohol or alcohols; and obtaining a ratio between the level of said alcohol or alcohols and the level of compound of Formula IIb.

According to another embodiment, the method may comprise the steps of:
removal of the carboxylic acid residues from compounds of Formula I in the sample to yield a compound of Formula Ib;

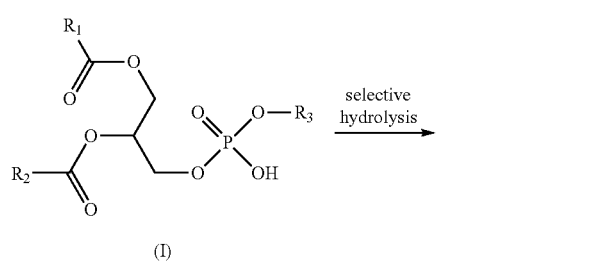

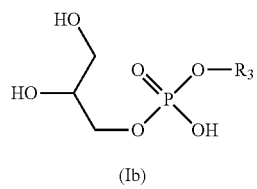

quantitatively determining the level of the compound of Formula Ib; and obtaining a ratio between the level of the compound of Formula Ib and the compound of Formula IIb; wherein the compound of Formula I is a bio-precursors of PEth selected from the group consisting of phosphatidyl serine, phosphatidyl ethanolamine, phosphatidyl inositol, cardiolipin and phosphatidyl choline. $R_1$ and $R_2$ may be independently selected from straight or branched $C_{9-39}$ alkyl, $C_{9-39}$ alkenyl, $C_{9-39}$ alkdienyl and $C_{9-39}$ alktrienyl, and $R_3$ may be selected from

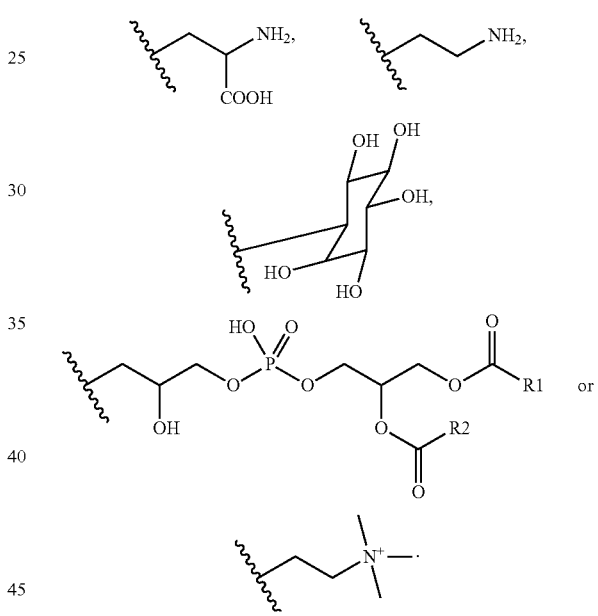

According to yet another aspect, a method is provided comprising the steps of: (i) obtaining a sample from the body of a subject; (ii) removal of the carboxylic acid residues of compounds of Formula II, i.e. PEth-homologues, present in the sample to yield a compound of Formula IIc by selective transesterification

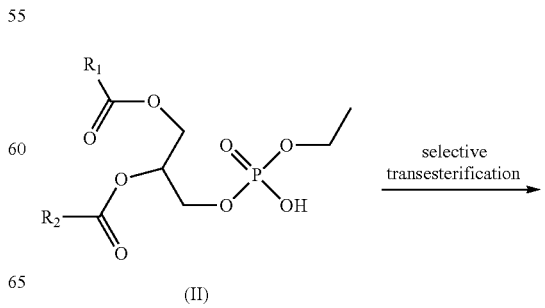

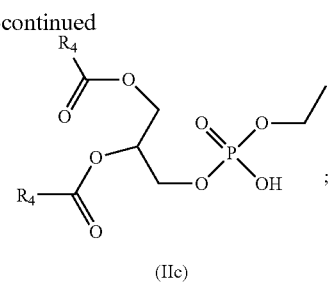

(IIc)

and (iii) quantitatively determining the level of the compound of Formula IIc; wherein the subject is a human or animal. At least one of R1 and R2, such as both of R1 and R2, may be different from R4. R1 may also be different from R2. Furthermore, R1 and R2 may be independently selected from straight or branched $C_{9-39}$ alkyl, $C_{9-39}$ alkenyl, $C_{9-39}$ alkdienyl and $C_{9-39}$ alktrienyl. $R_4$ may be a saturated or unsaturated straight carbon chain, or the carboxylic acid residue of a synthetically produced carboxylic acid.

According to another embodiment, the method may further comprise the steps of: exchange of the carboxylic acid residues covalently bound as esters in one or several bio-precursors of PEth by selective transesterification to yield the corresponding transesterified ester or esters; quantitatively determining the level of the transesterified ester or esters; and obtaining a ratio between the level of the transesterified ester or esters and the level of compound of Formula IIb.

According to another embodiment, the method may further comprise the steps of: removal of the carboxylic acid residues from compounds of Formula I present in the sample to yield a compound of Formula Ic by selective transesterification;

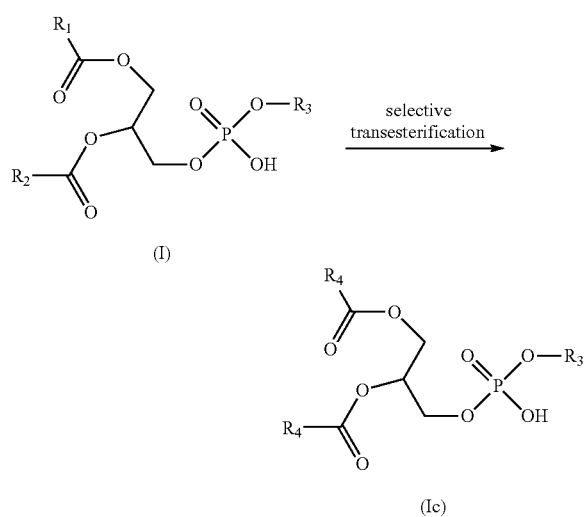

(Ic)

quantitatively determining the level of the compound of Formula Ic; and obtaining a ratio between the level of the compound of Formula Ic and the compound of Formula IIc; wherein the compound of Formula I is a bio-precursors of PEth selected from the group consisting of phosphatidyl serine, phosphatidyl ethanolamine, phosphatidyl inositol, cardiolipin and phosphatidyl choline. At least one of R1 and R2, such as both of R1 and R2, may be different from R4. R1 may also be different from R2. $R_1$ and $R_2$ may be independently selected from straight or branched $C_{9-39}$ alkyl, $C_{9-39}$ alkenyl, $C_{9-39}$ alkdienyl and $C_{9-39}$ alktrienyl. R4 may be a saturated or unsaturated straight carbon chain, or the carboxylic acid residue of a synthetically produced carboxylic acid. $R_3$ may be selected from

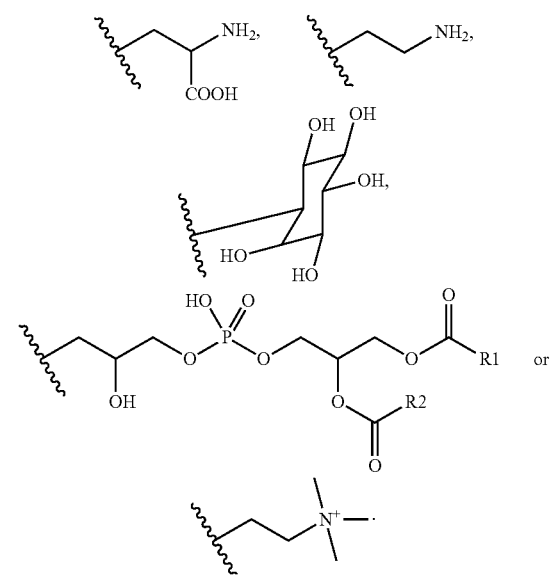

According to another embodiment, all substituents R4 of compounds of Formula Ic may be the same as all substituents R4 of compounds of Formula IIc.

According to another embodiment, R4 of compounds of formula Ic or IIc may comprise one or several UV-absorbing groups, such as 6- or 5-membered aromatic rings or condensed aromatic systems.

According to yet another aspect, a method is provided for assessment of previous absolute ethanol consumption in a subject comprising the steps of: (i) obtaining a first measure of previous ethanol exposure in the subject according to, for example, any of above mentioned methods; (ii) obtaining a second measure of previous ethanol exposure in at least one reference according to, for example, any of above mentioned methods; and (iii) comparing the first measure with the second measure; wherein the first measure is obtained by a method which is the same as the method by which the second measure is obtained; and the at least one reference is a human or animal which has been exposed to a known amount of ethanol prior to obtaining a sample used for obtaining the second measure.

Further features of the invention and its embodiments are set forth in the appended claims.

BRIEF DESCRIPTION OF THE DRAWINGS

These and other aspects, features and advantages of which the invention is capable will be apparent and elucidated from the following description of non-limiting embodiments of the present invention, reference being made to the accompanying drawings, in which.

DETAILED DESCRIPTION OF THE EMBODIMENTS

Figure 1:
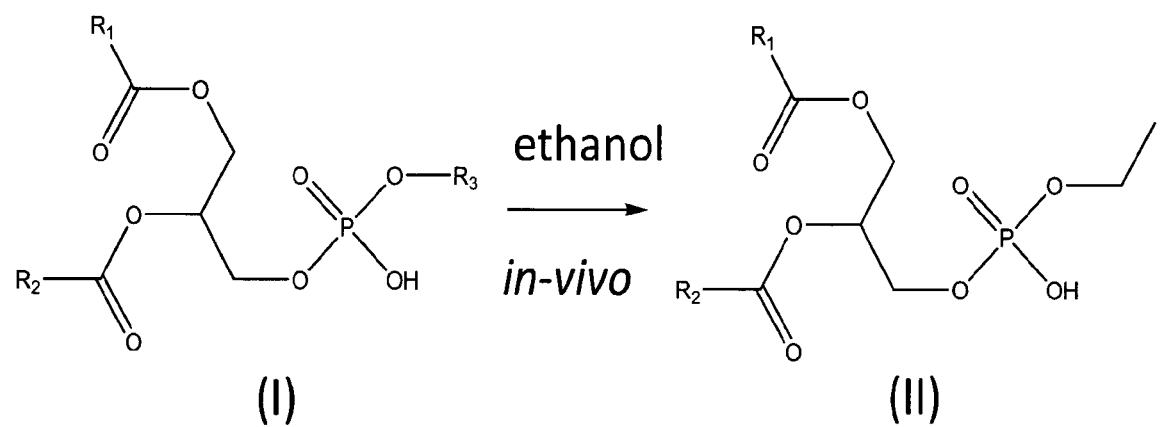
FIG. 1 is a reaction scheme showing the bio-transformation of bio-precursors (I) of PEth into the corresponding PEth-homologues, the latter being ethanol bio-markers.

Embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Embodiments of the present invention will now be described below with reference to FIGS. 1 to 7.

The present invention utilizes a measure as indicative of previous ethanol exposure. This measure is dependent on the level of at least one biomarker and the level of at least one PEth-homologue or ethylsfingomyelin-homologue, wherein the latter is dependent on the former. The biomarker may be one or several bio-precursors of PEth or ethylsfingomyelin, an amount of cellular material, or another set of at least one PEth-homologue. Such a measure, like e.g. a ratio between a specific PEth-homologue and its corresponding phosphatidyl choline bio-precursor, may reflect previous alcohol consumption more accurately than the concentration of the specific PEth-homologue or the sum of several PEth-homologues.

Many medical conditions or diseases are caused or aggravated by alcohol abuse. An objective and reliable quantitative measure of previous alcohol consumption would be of great help in the investigation and evaluation of these conditions or diseases. A reliable measure of alcohol consumption is also of value in for example workplace testing and in legal issues particularly in working life and in driving license issues.

Measures of the present invention will more accurately reflect previous ethanol exposure, with a minimized risk of false positive or negative results, as compared to other measures of the prior art, typically the concentration of a specific PEth-homologue or the sum of several PEth-homologues in a sample from a subject.

We have found that the ratio between bio-precursors, like phosphatidyl choline, and the corresponding bio-markers, like PEth, may be used for assessment of bio-marker associated events, like previous ethanol intake, with improved level of confidence.

Intra-individual variability and inter-individual variability, such as variability over time, in the substitution pattern of a homologues series of bio-precursors, results in the same or a similar variability of the corresponding bio-markers if the substituents causing the homology are left unaffected in the corresponding bio-chemical transformation. Factors which may be the underlying cause and affecting the magnitude of such variability include diet, i.e. eating habits, ethnic origin, diseases, stress level, previous alcoholism, age and sex.

For example, the level of phosphatidyl choline homologues carrying linoleic acid (18:2), as one of the carboxylic acid substituents, was found to increase significantly in healthy adults when they switched from a diet high in saturated fat to a diet high in polyunsaturated fat (Skeaff et al, J. Nutr. 2006, 136, 565-9). Since phosphatidyl choline is a bio-precursor of PEth, the level of PEth-homologues comprising e.g. linoleic acid (18:2) or oleic acid (18:1), such as the commonly occurring PEth 16:0/18:2 and PEth 16:0/18:1, is dependent on a persons eating habit.

In another example, the relative fractions of the PEth-homologues 18:1/18:1, 16:0/16:0 and 16:0/18:2 were reported to be positively correlated with a relatively high consumption of ethanol (H. Gnann et al Anal. Bioanal. Chem. 2010, 396, 2415-2423; A. Helander et al Clin. Chem. 2009, 55, 1395-405).

Hence, the level of previous ethanol intake may be over- or underestimated depending on e.g. a persons eating habits and/or presence or absence of previous alcoholism, when methods of the prior-art, which employ PEth quantification, are used.

According to one aspect, the present invention provides a method for determination of previous ethanol exposure, such as consumption, essentially comprising determination of the ratio between the concentration of an ethanol bio-marker and the corresponding bio-precursor in a sample, such as a blood sample, from a person or animal. By correlating such a ratio, obtained by analysis of samples from subjects, e.g. humans, with known previous ethanol consumption or exposure of these subjects, a correlation factor or graph may be obtained. This correlation factor or graph may be used to assess previous ethanol consumption in a subject by (i) analysis of a sample taken from the subject, (ii) determination of above mentioned ratio and (iii) comparison of this ratio with the correlation factor or graph.

Advantages of the method according to the invention include a minimized risk for overestimation or underestimation of a person's previous ethanol consumption.

According to one embodiment, the ethanol bio-precursor may be a singularity or plurality of endogenous molecules, or a singularity or plurality of homologues thereof, which form PEth under the influence of ethanol. The bio-marker may be PEth or a singularity or plurality of PEth-homologues.

According to one embodiment, the ratio may be a ratio between the concentration or amount of one bio-precursor of PEth in a sample and the concentration or amount, respectively, of one PEth-homologue in the same sample.

According to one embodiment, the ratio may be a ratio between the concentration or amount of one PEth-homologue in a sample and the concentration or amount, respectively, of one bio-precursor of PEth in the same sample.

According to one embodiment, the ratio may be a ratio between the sum of concentrations or the sum of amounts of at least two bio-precursors of PEth in a sample and the sum of concentrations or the sum of amounts, respectively, of at least two PEth-homologues in the same sample.

According to one embodiment, the ratio may be a ratio between the sum of concentrations or the sum of amounts of at least two PEth-homologues in a sample and the sum of concentrations or the sum of amounts, respectively, of at least two bio-precursors of PEth in the same sample.

According to one embodiment, the bio-precursor may be a singularity or plurality of compounds of Formula I, or any charged or stereoisomeric form thereof. The bio-marker may be a singularity or plurality of the corresponding compounds of Formula II, or any charged or stereoisomeric form thereof, formed by reaction of compounds of Formula I with ethanol in-vivo, according to the reaction depicted in FIG. 1. Preferably, R1 and R2 in Formula I and II are represented by the carbon chains of endogenous carboxylic acids or esters. Preferably, R3 in Formula I is represented by the corresponding substituents in endogenous phospholipids such as phosphatidyl serine, phosphatidyl ethanolamine, phosphatidyl inositol or phosphatidyl glycerol (cardiolipin), and more preferred by the corresponding substituent in phosphatidyl choline.

According to one embodiment, the bio-precursor may be sphingomyelin and the bio-marker may be the corresponding compound or compounds, i.e. homologues with different carboxylic acid residues, in which the choline residue of the sphingomyelin has been replaced by ethanol to yield ethyl-sphingomyelin homologues, analogously to the reaction of scheme 1.

According to one embodiment, the ratio is formed by dividing the concentration of one bio-marker in a sample with the concentration of the corresponding bio-precursor in the same sample. Preferably, the bio-marker and bio-precursor are selected such that they represent one of the more commonly occurring, preferably the most commonly occurring, homologues if belonging to a group of homologues.

According to one embodiment, the ratio is formed by dividing the sum of the concentrations of at least two bio-markers in a sample with the sum of the concentrations of the corresponding bio-precursors in the same sample.

According to one embodiment, the bio-precursor may be one or several endogenous phospholipids comprising carboxylic acids covalently bond by ester or amide bonds. The carboxylic acids are preferably selected from the group consisting of carboxylic acids comprising 14 to 30 carbon atoms with 0 to 4 double bonds, like palmitic acid, stearic acid, oleic acid, linoleic acid, arachidonic acid and pentadecanoic acid. More preferred are carboxylic acids with 16, 18 or 20 carbon atoms and with 0, 1, 2 or 4 double bonds. Most preferred are bio-precursors which are transformed in-vivo into PEth 16:0/18:1, PEth 16:0/18:2, PEth 16:0/20:4, PEth 18:0/18:1, PEth 18:1/18:1 and PEth 18:0/18:2, or the corresponding homologues, i.e. regioisomers, in which the carboxylic acid residues have switched places on the glycerol backbone.

According to one embodiment, the bio-marker may be one or several PEth-homologues comprising carboxylic acids covalently bond by ester bonds. The carboxylic acids are preferably selected from the group consisting of carboxylic acids comprising 14 to 30 carbon atoms with 0 to 4 double bonds, like palmitic acid, stearic acid, oleic acid, linoleic acid, arachidonic acid and pentadecanoic acid. More preferred are carboxylic acids with 16, 18 or 20 carbon atoms and with 0, 1, 2 or 4 double bonds. Most preferred are PEth 16:0/18:1, PEth 16:0/18:2, PEth 16:0/20:4, PEth 18:0/18:1, PEth 18:1/18:1 and PEth 18:0/18:2, or the corresponding homologues, i.e. regioisomers, in which the carboxylic acid residues have switched places on the glycerol backbone.

According to another aspect, the ratio between one or several PEth-homologues and a measurable parameter representing an amount of cellular material may be used for assessment of biomarker associated events, like previous ethanol intake, with improved level of confidence. Intra-individual and inter-individual variability in cellular material in a sample results in the same or similar variability of the biomarker for ethanol intake. For example a sample containing low amounts of cellular material would be expected to contain lower amounts of the biomarker for ethanol, e.g. PEth or one or several PEth-homologues, than a sample with a high content of cellular material. Hence, the level of previous ethanol intake may be over- or underestimated depending on e.g. the amount of cellular material in the sample, when methods of the prior-art, which rely solely on PEth quantification are used. The present invention provides an improved method in comparison to methods which rely solely on determination of one or several PEth-homologues. The method of the invention is comprising the following steps: (i) obtaining a sample of the blood of a human being or animal, (ii) determining the level of a measurable parameter, e.g. haemoglobin or the erythrocyte volume fraction (EVF), or any other parameter known in the art which is representing the amount of cellular material in the blood sample, (iii) determining an amount, level or concentration of one or several biomarkers of ethanol in the blood sample, (iv) determining a ratio between the measurable parameter and the amount, level or concentration of one or several biomarkers of ethanol, e.g. one or several PEth-homologues. When more that one biomarker, such as PEth-homologues, are quantitatively determined, their sum may be used for obtaining a ratio between these and the measurable parameter. A ratio between the amount, level or concentration of one or several biomarkers of ethanol and the measurable parameter, may be obtained in step (iv). Either of the ratios thus obtained are correlating to the previous ethanol intake with a lower risk for false positives or negatives than methods of the prior art which rely solely on measurement of one or several PEth-homologues. By correlating such a ratio obtained by analysis of samples from subjects, e.g. humans, with known previous ethanol consumption or exposure of these subjects, a correlation factor or graph may be obtained.

According to yet another aspect, the invention provides a method for assessment of e.g. the history of previous ethanol intake. A first bio-marker/bio-precursor ratio may be compared with a second bio-marker/bio-precursor ratio or with the level of a bio-marker. If the bio-marker of the second bio-marker/bio-precursor ratio or the bio-marker has a different half-life in-vivo than the bio-marker of the first bio-marker/bio-precursor ratio, important conclusions may be drawn. Such conclusions include conclusions regarding the amount of e.g. previously consumed ethanol, as well as e.g. the time span since that amount was consumed.

According to one embodiment, the bio-marker of the first bio-marker/bio-precursor ratio is PEth. The bio-marker of the second bio-marker/bio-precursor ratio or the bio-marker may be selected from the group consisting of ethanol, ethyl glucuronide, ethyl sulfate, ethyl phosphate, gamma-glutamyl-transferase, carbohydrate-deficient transferrin, fatty acid ethyl esters and PEth.

According to one embodiment, the level of PEth in blood and the level of PEth in plasma may be compared in order to draw conclusions regarding e.g. the amount of previously consumed ethanol, as well as e.g. the time span since that amount was consumed.

Figure 2:
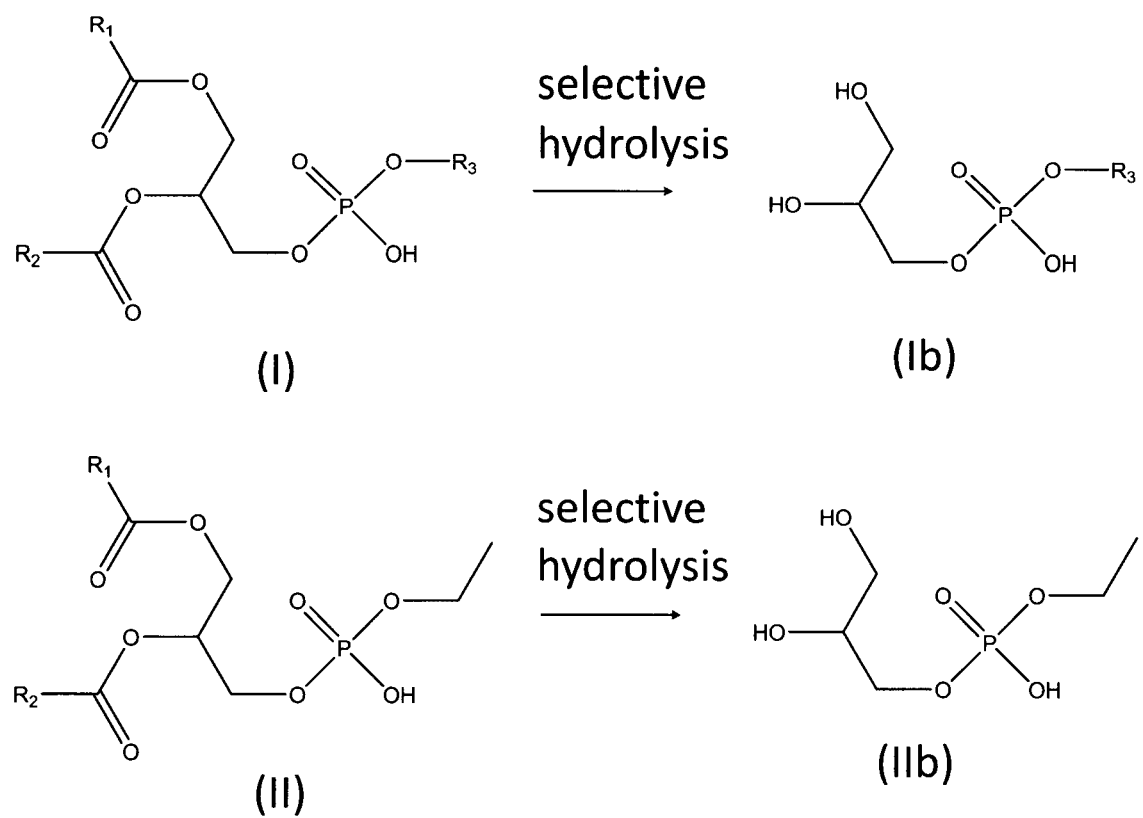
FIG. 2 is a reaction scheme showing the selective hydrolysis of the carboxylic acid residues of bio-precursors of PEth (Formula I) into the corresponding free diols (Formula Ib), and the selective hydrolysis of the carboxylic acid residues of PEth-homologues (Formula II) into the corresponding free diol (Formula IIb), according to an embodiment of the invention.
Figure 3:
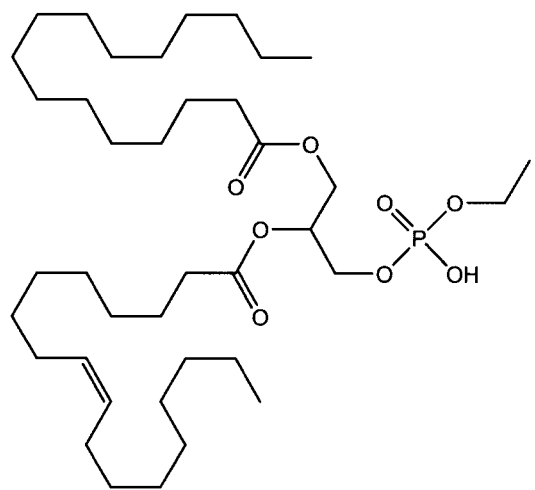
FIG. 3 is showing the structures of two commonly occurring PEth-homologues, PEth 16:0/18:1 and PEth 16:0/18:2, wherein oleic acid and linoleic acid serves as examples of possible carboxylic acid residues corresponding to the 18:1 part and the 18:2 part, respectively.
Figure 3:
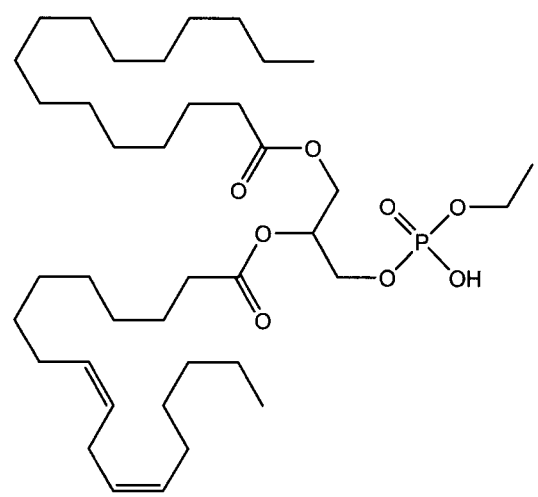

According to yet another aspect, the present invention provides a method for determination of previous ethanol exposure, such as consumption, essentially comprising selective removal of one (not shown in FIG. 2) or both, preferably both, of the carboxylic acid residues of PEth and/or the corresponding bio-precursors, as shown in FIG. 2. A sample, such as a blood sample, from a subject, such as a person may be (i) treated under suitable conditions for selective hydrolysis of the carboxylic acid residues of compounds of Formula I and/or II, followed by (ii) quantification of the respectively obtained compounds of Formula Ib and/or IIb. For example, the carboxylic acid residues covalently bound as esters in one or several bio-precursors of PEth, such as the corresponding phosphatidyl serine, phosphatidyl ethanolamine, phosphatidyl inositol or phosphatidyl choline, may be removed by selective hydrolysis to yield the corresponding alcohol or alcohols. The level, i.e. the concentration, of one or several of these alcohols, such as the alcohol derived from the corresponding phosphatidyl choline, may then be determined by a suitable method, such as HPLC-MS/MS analysis of a pre-treated blood-sample. This level may then be compared with the corresponding level of a compound of Formula IIb, preferably but not necessarily formed in the same sample and in parallel with the formation of the alcohol or alcohols derived from bio-precursors of PEth. A measure indicative of previous ethanol exposure in the form of a ratio between the levels may, for example, be calculated.

The herein before mentioned disadvantages associated with the assessment of previous ethanol consumption by quantification of one or several PEth-homologues by methods of the prior-art, are eliminated by the solution according to the invention. The, in step (i), generated compounds of Formula Ib or IIb quantitatively represents the sum of the homologues of Formula I or II, respectively. Independent of method used (e.g. electrophoretic, chromatographic, spectrometric, mass spectrometric, electrochemical, enzymatic and immunochemical methods or the like), the quantification of compound of Formula Ib or IIb may be performed more easily than the quantification of one or several of the homologues of formula I or II. Such quantification of compound of Formula Ib or IIb may, for example, be made by employment of HPLC-ELS, HPLC-MS or the like.

Methods for selective hydrolysis of the carboxylic acid residues of compounds of Formula I and/or II are known to the one skilled in the art.

According to one embodiment, $R_1$ and $R_2$ of compounds of Formula I may be independently selected from straight or branched $C_{9-39}$ alkyl, $C_{9-39}$ alkenyl, $C_{9-39}$ alkdienyl and $C_{9-39}$ alktrienyl. Esters comprising these substituents may be hydrolysed by selective hydrolysis.

According to one embodiment, $R_3$ of compounds of Formula I and Ib may be selected from

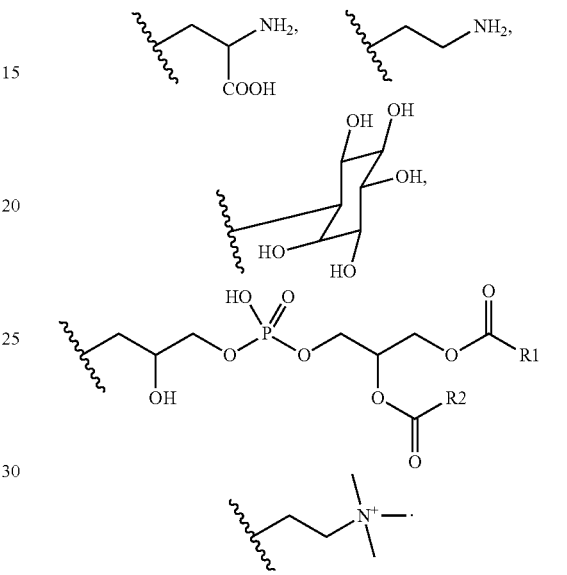

According to one embodiment, assessment of previous ethanol consumption may be done by correlating the concentration of the compound of Formula IIb, after selective hydrolysis of the carboxylic acid residues of homologues of Formula II in samples from subjects, e.g. humans, with known previous ethanol consumption or exposure of these subjects, to obtain a correlation factor or graph. This correlation factor or graph may be used to assess previous ethanol consumption in a subject by (i) selective hydrolysis of the carboxylic acid residues of homologues of Formula II in a sample from the subject to yield the compound of Formula IIb, followed by (ii) quantification of IIb and (iii) comparison of the obtained concentration with the correlation factor or graph.

According to one embodiment, assessment of previous ethanol consumption may be done based on the ratio between the concentration of Ib and IIb, or IIb and Ib, as described herein and in analogy to the ratio between I and II, or II and I.

According to one embodiment, the selective hydrolysis of the carboxylic acid residues of compounds of Formula I and/or II may be performed by use of a hydrolase selected from the group consisting of pancreatic triacylglycerol lipases, lipoprotein lipases, lingual lipases, monoacylglycerol lipases, diacylglycerol lipases, hepatic lipases and triglyceride lipases.

According to one embodiment, the selective hydrolysis of the carboxylic acid residues of compounds of Formula I and/or II may be performed by use of *Rhizomucor miehei* lipase, phospholipase A1, phospholipase A2, or mixtures thereof.

Figure 4:
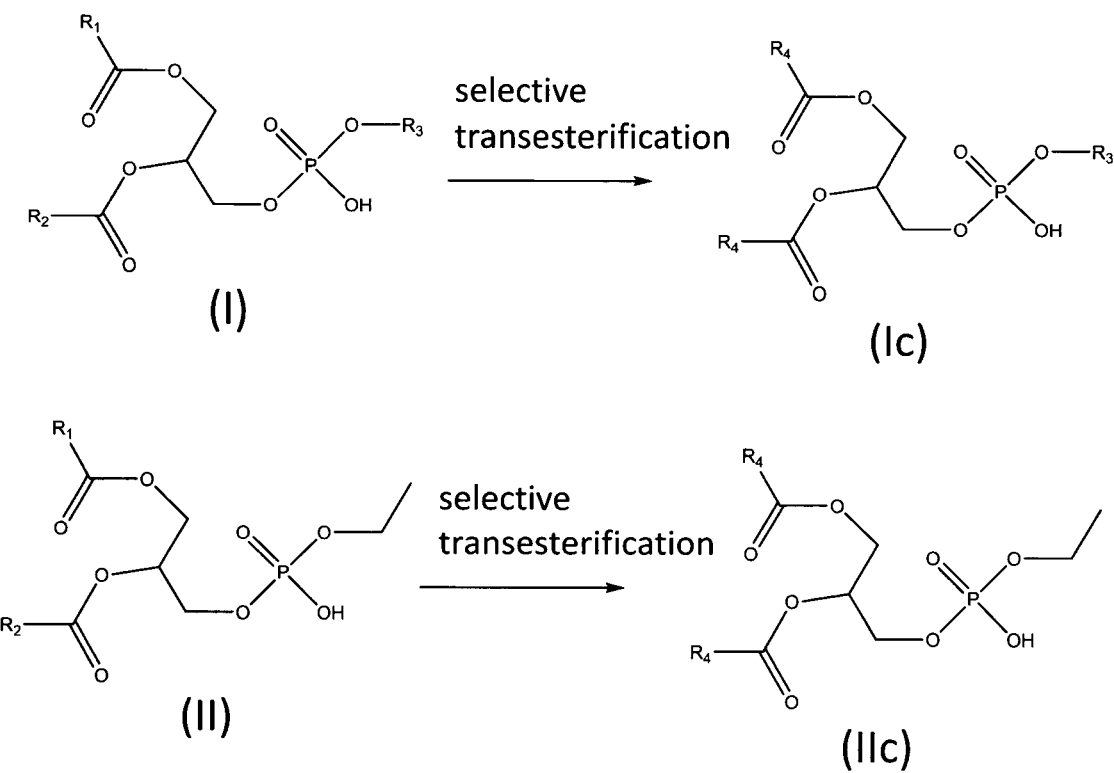
FIG. 4 is a reaction scheme showing the selective transesterification of compounds of formula I, i.e. bio-precursors of PEth, and compounds of formula II, i.e. PEth-homologues, into compounds of formula Ic and IIc, respectively, according to an embodiment of the invention.
Figure 5:
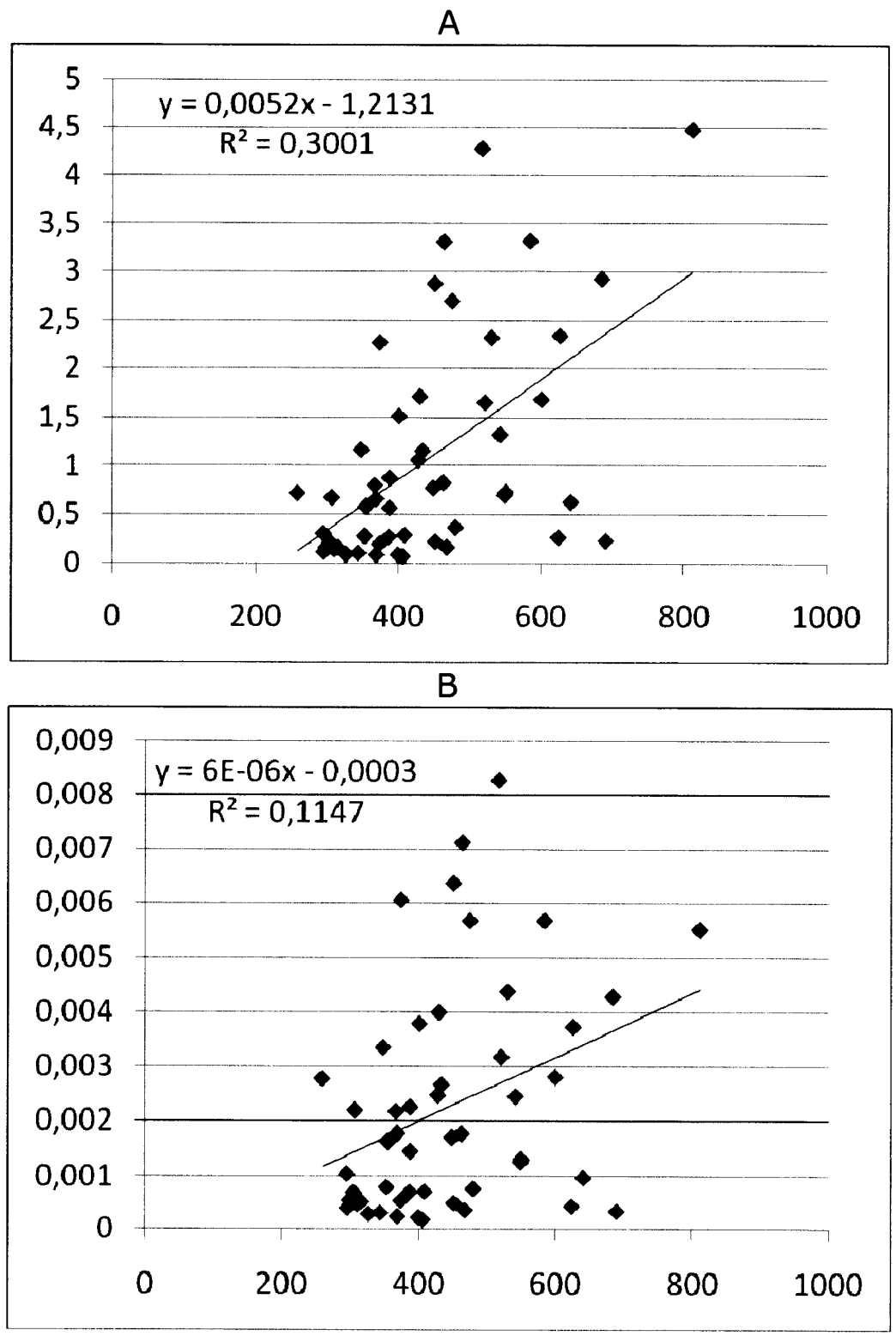
FIG. 5 shows different graphs of data generated by analysis of 50 blood samples from randomly selected persons, wherein the upper graph (A) shows the concentration of PEth 16:0/18:1 (µmol/L) on the y-axis versus the concentration of the corresponding phosphatidyl choline bio-precursor (PC16:0/18:1, µmol/L) on the x-axis, and the lower graph (B) shows the ratio between the concentration of PEth 16:0/18:1 (µmol/L) and the concentration of the corresponding phosphatidyl choline bio-precursor (PC16:0/18:1, µmol/L) on the y-axis versus the concentration of the corresponding phosphatidyl choline bio-precursor (PC16:0/18:1, µmol/L) on the x-axis.
Figure 6:
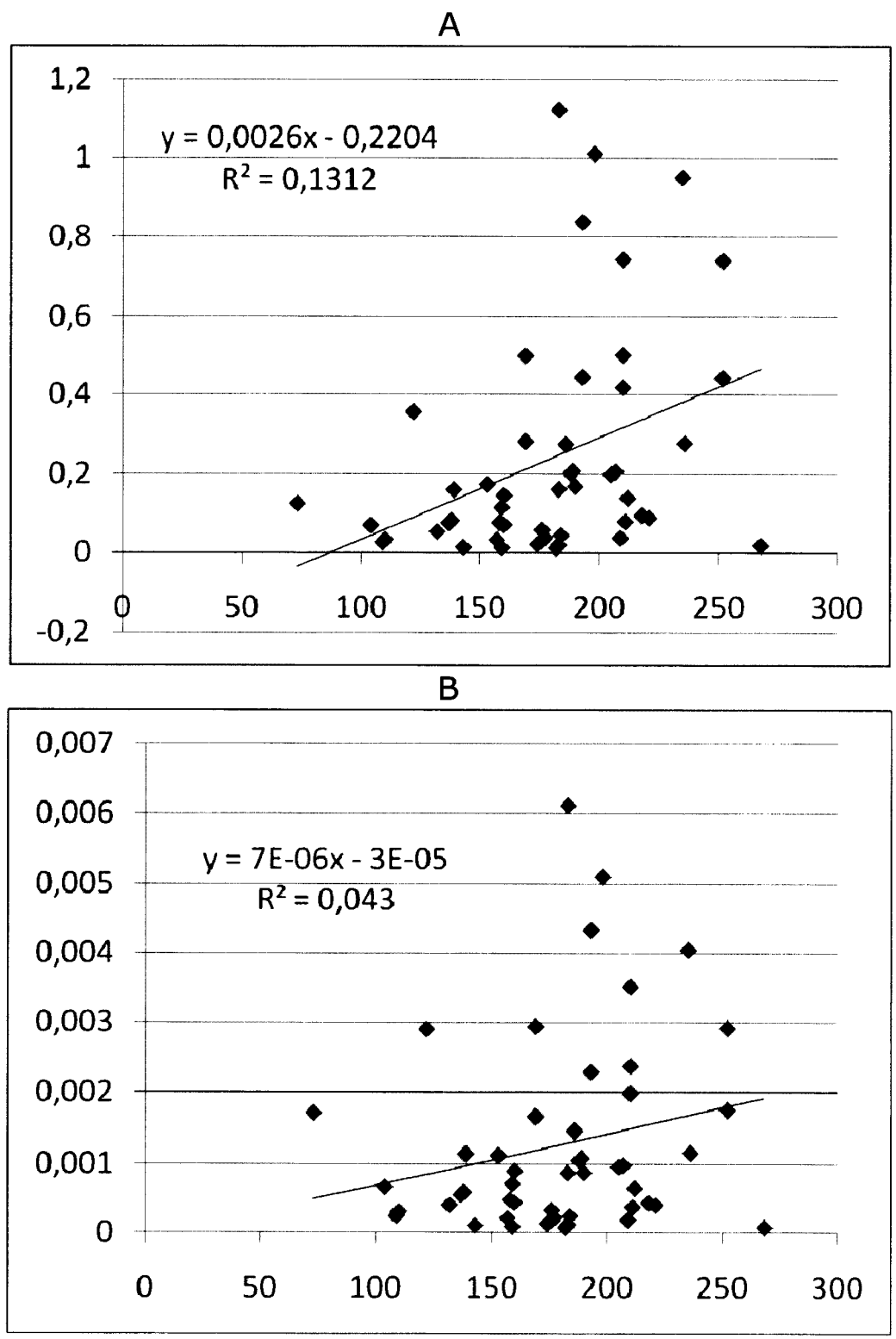
FIG. 6 shows different graphs of data generated by analysis of 50 blood samples from randomly selected persons, wherein the upper graph (A) shows the concentration of PEth 16:0/20:4 (µmol/L) on the y-axis versus the concentration of the corresponding phosphatidyl choline bio-precursor (PC16:0/20:4, µmol/L) on the x-axis, and the lower graph (B) shows the ratio between the concentration of PEth 16:0/20:4 (µmol/L) and the concentration of the corresponding phosphatidyl choline bio-precursor (PC16:0/20:4, µmol/L) on the y-axis versus the concentration of the corresponding phosphatidyl choline bio-precursor (PC16:0/20:4, µmol/L) on the x-axis.
Figure 7:
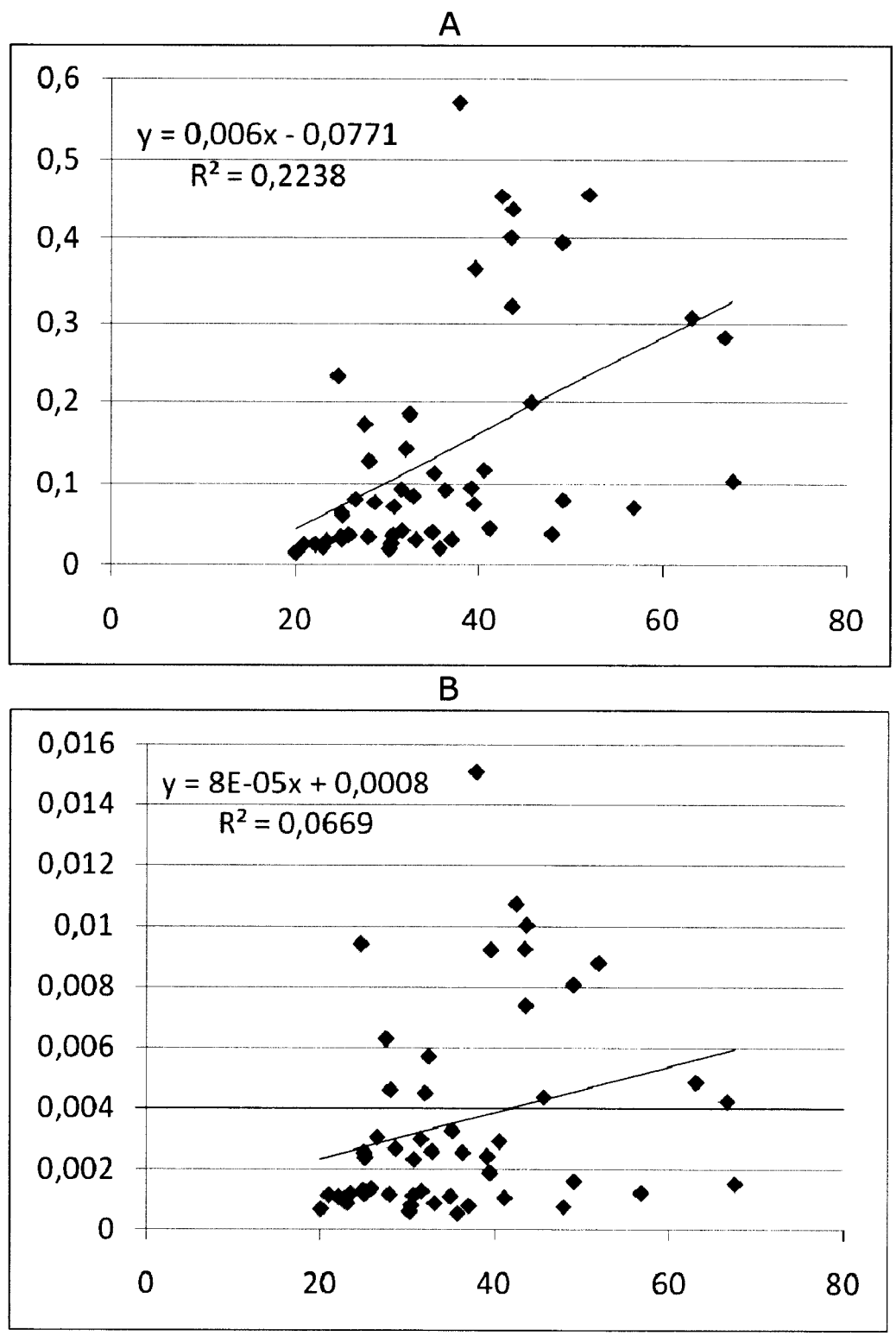
FIG. 7 shows different graphs of data generated by analysis of 50 blood samples from randomly selected persons, wherein the upper graph (A) shows the concentration of PEth 18:1/18:1 (µmol/L) on the y-axis versus the concentration of the corresponding phosphatidyl choline bio-precursor (PC18:1/18:1, µmol/L) on the x-axis, and the lower graph (B) shows the ratio between the concentration of PEth 18:1/18:1 (µmol/L) and the concentration of the corresponding phosphatidyl choline bio-precursor (PC18:1/18:1, µmol/L) on the y-axis versus the concentration of the corresponding phosphatidyl choline bio-precursor (PC18:1/18:1, µmol/L) on the x-axis.

According to yet another aspect, the present invention provides a method for determination of previous ethanol exposure, such as consumption, essentially comprising selective transesterification of the carboxylic acid residues of PEth-homologues II and/or the corresponding bio-precursors I, as shown in FIG. 4. The carboxylic acid residues of I and/or II are thereby substituted by one uniform carboxylic acid residue which carries R4. Applications and advantages of the resulting compounds of formula Ic and IIc are analoguous to the applications and advantages of the corresponding compounds of formula Ib and IIb, as described in embodiments herein. For example, the same ester side chains of e.g. PEth homologues or PEth bio-precursors that may be removed by selective hydrolysis, may also be replaced by another ester side chain by selective transesterification. At least one of R1 and R2 of compounds of Formula I or II, such as both of R1 and R2, may be different from R4 of compounds of Formula Ic and IIc, respectively. R1 may also be different from R2. R4 of the transesterified product of Formula Ic or IIc may be a saturated or unsaturated straight carbon chain, or the carboxylic acid residue of a synthetically produced carboxylic acid.

According to one embodiment, the method comprising selective transesterification may comprise the steps of: exchange of the carboxylic acid residues covalently bound as esters in one or several bio-precursors of PEth by selective transesterification to yield the corresponding transesterified ester or esters; quantitatively determining the level of the transesterified ester or esters; and obtaining a ratio between the level of the transesterified ester or esters and the level of compound of Formula IIb.

According to one embodiment, the carboxylic acid residue comprising R4 may be an endogenous carboxylic acid.

According to one embodiment, R4 may be a saturated or unsaturated straight carbon chain and the same as one the corresponding carbon chains of a PEth-homologue. Hence, R4 may be the same as one of R1 or R2.

According to one embodiment, the carboxylic acid residue comprising R4 may be a synthetically produced carboxylic acid or precursor thereof.

According to one embodiment, R4 may comprise UV-absorbing groups as known in the art. Examples of such groups include aromatic 6- or 5-membered aromatic rings, such as phenyl, pyridyl, thienyl and furanyl, and condensed aromatic systems, such as naphtyl or indolyl. Advantages of the inclusion of UV-absorbing groups in R4 include the possibility to detect compounds Ic and/or IIc, when quantitatively determining the same, by commonly occurring and relatively uncomplicated UV-detectors. R4 may also comprise other groups, as known in the art, which make Ic and IIc detectable by other types of detectors, such as e.g. fluorescence detectors, for quantification of Ic and/or IIc.

According to one embodiment, the selective transesterification of the carboxylic acid residues of compounds of Formula I and/or II may be performed by use of a hydrolase selected from the group consisting of pancreatic triacylglycerol lipases, lipoprotein lipases, lingual lipases, monoacylglycerol lipases, diacylglycerol lipases, hepatic lipases and triglyceride lipases, in the presence of an excess of R4COOH or an active ester or similar thereof.

According to one embodiment, the selective transesterification of the carboxylic acid residues of compounds of Formula I and/or II may be performed by use of *Rhizomucor miehei* lipase, phospholipase A1, phospholipase A2, or mixtures thereof, in the presence of an excess of R4COOH or an active ester or similar thereof.

According to one embodiment, the stereochemistry of the chiral center of the glycerol-backbone of compounds of formula I, Ib, II, IIb, Ic and IIc may be the naturally occurring "R".

According to yet another aspect, a method is provided for assessment of previous absolute ethanol consumption in a subject comprising the steps of: (i) obtaining a first measure of previous ethanol exposure in the subject; (ii) obtaining a second measure of previous ethanol exposure in at least one reference; and (iii) comparing the first measure with the second measure. The first and second measure may be any measure disclosed herein which is indicative of previous ethanol exposure such as, for example, the ratio between the level of one or several PEth-homologues and one or several of the corresponding bio-precursors of PEth, such as phosphatidyl choline, in a blood sample from the subject or the reference. Additional examples of such measures include the level, e.g. the concentration in a blood sample from the subject or reference, of compounds of Formula IIb or IIc after selective hydrolysis or transesterification, respectively. The first and second measures are preferably obtained by the same method to facilitate the comparison between these measures. The subject and reference are preferably of the same species, such as human or animal, for the same reason. The subject and the reference may, however, be of different species if a suitable translational model as known in the art is available. The reference may first be kept unexposed to ethanol for a sufficient time, such as at least 2 weeks or preferably more than 2 months, to allow essentially full clearance of relevant biomarkers of ethanol, such as PEth-homologues. The reference may then be exposed, such as orally or by IV injection, to a known amount of ethanol before collection of e.g. a blood sample which may be analyzed to obtain the second measure. This amount is preferably related to the weight of the reference such that the unit by which the reference has been exposed may be measured in e.g. "gram ethanol/kg". The reference may also be repeatedly exposed to ethanol, such as once or twice per day, such that the unit by which the reference has been exposed may be measured in e.g. "gram ethanol/kg*day". Repeated exposure of ethanol is preferably continued for a time until a steady-state of the relevant biomarker, such as one or several PEth-homoloues, has been reached. The time needed to reach such steady state may easily be calculated or determined by the one skilled in the art. The second measure is thereby related to a known previous absolute ethanol consumption of the reference. The first measure is, in an analogous way, related to a previous absolute ethanol consumption of the subject. The previous absolute ethanol consumption of the subject may be estimated or calculated by comparing the first measure with the second measure. Several references may be exposed to various doses of ethanol in order to obtain e.g. a calibration curve, from which the previous absolute ethanol consumption of a subject may be calculated in an accurate way.

Quantification of compounds of formula I, Ib, II, IIb, Ic and IIc in samples, such as blood samples, may be performed by well known analytical methods, devices and techniques including, for example, electrophoretic, chromatographic, spectrometric, mass spectrometric, electrochemical, enzymatic and immunochemical methods. Specific examples of such techniques include HPLC-MS, HPLC-MS/MS, HPLC-UV and HPLC-ELS.

EXAMPLES

Below follows non-limiting examples on provision of measures which are indicative of previous ethanol exposure, according to the invention.

General Methods Used in the Examples Below for Quantification of Phosphatidyl Choline Homologues (PC Homologues) and Phosphatidyl Ethanol Homologues (PEth Homologues) in Blood Samples Lipids for analysis of PEth homologues were extracted from 200 μL whole blood by drop wise adding the blood to 1.4 mL 2-propanol that contained 0.057 μmol/L phosphatidyl propanol (internal standard) under agitation on a mixer. Subsequently, 1.8 ml hexane was added to the extract and again mixed for one minute. The extract was centrifuged at 1500×g for ten minutes, after which the supernatant was evaporated under nitrogen at 37° C. until complete dryness, and finally dissolved in 400 μL 2-propanol/methanol (50/50) to yield a PEth-extract. Lipids for analysis of PC homologues were extracted from 200 μL diluted whole blood (diluted 1/77 with saline) and thereafter processed as the undiluted blood, to yield a PC-extract. The PEth and the PC-extract were analyzed with Liquid Chromatography triple quadrupole mass spectrometry (HPLC-MS/MS). Five μL was injected with an injector from CTC Analytics (CTC Analytics AG Industriestrasse 20CH-4222 Zwingen Switzerland, www.palsystem.com). Lipids were separated with reversed phase chromatography by binary gradient elution. The gradient was formed by pumps (LC-20AD XR) from Shimadzu Corporation, Kyoto, Japan (www.shimadzu.com). The lipids were quantified with a triple quadrupole mass spectrometer from Sciex, Canada (API 4000, www.absciex.com) equipped with the company's electro spray ion (ESI) source (TURBO V™ source) working in the negative mode. The SMR mode (Selected Reaction Monitoring, www.ionsource.com/tutorial/msquan/intro.htm) was utilized for quantification. The tuning for the SRM was done by using pure standards of PEth and PC homologues with the fatty acid residues 16:0/18:1, 16:0/20:4 and 18:1/18:1. The parent mass for the PEth homologues are the unprotonated molecular ion [M–H]$^-$ and for PC homologues, the unprotonated formate adduct of the molecular ion [M+HCOO$^-$]$^-$. The fragments mass used for quantification were in all cases the unsaturated fatty acid ion.

Examples 1 to 3

Examples 1 to 3 are comparative examples showing that a measure in the form of the ratio of the concentration of various PEth-homologues and their corresponding bio-precursors is less dependant on the concentration of the bio-precursor than the concentration of the corresponding PEth-homologue. Hence, these examples support that a measure in the form of the ratio of the concentration of various PEth-homologues and their corresponding bio-precursors is less dependent on parameters which are not related to previous alcohol intake, than the concentration of the corresponding PEth-homologue. Parameters not related to previous alcohol intake include e.g. a person's eating habits. A measure in the form of the ratio of the concentration of various PEth-homologues and their corresponding bio-precursors is therefore a predictor of previous alcohol intake with a minimized risk for erroneous conclusion regarding this intake in comparison to a predictor in the form of the concentration of one or several PEth-homologues.

In Examples 1 to 3, blood-samples were collected from 50 randomly selected persons, i.e. with various eating and drinking habits. The concentrations of various PEth-homologues and their corresponding phosphatidyl choline bio-precursors in these samples were determined by HPLC-MS/MS. The concentration of each PEth-homologue was plotted against the concentration of the corresponding phosphatidyl choline bio-precursor. Also, the ratio between the concentration of each PEth-homologue and the concentration of the corresponding phosphatidyl choline bio-precursor was plotted against the concentration of the phosphatidyl choline bio-precursor. Each dataset was analyzed in accordance with statistical methods well known in the art. A linear regression model was fitted to each dataset using the least squares approach to determine the coefficients "k" and "m" of the equation "y=kx+m" (wherein "y" is the concentration of the PEth-homologue or the ratio between the concentration of the PEth-homologue and the concentration of the corresponding phosphatidyl choline and "x" is the concentration of the corresponding phosphatidyl choline), which best describes the data. An "R-squared" ($R^2$) value was calculated for each model by the equation "R-squared=1–(the residual sum of squares/the total sum of squares). The R-squared value is indicative of how well the model describes the data, i.e. a high R-squared value indicates a better fit of the model and that "y" is more dependant on "x" than a lower R-squared value.

Example 1

A dataset consisting of the concentration of PEth 16:0/18:1 (C-PEth16:0/18:1), the concentration of the corresponding phosphatidyl choline bio-precursor (C-PC16:0/18:1), and the ratio (PEth/PC) between the concentration of PEth 16:0/18:1 and the concentration of the corresponding phosphatidyl choline bio-precursor, was collected by the analysis of the 50 samples as described above. The specific values of the dataset are depicted in the table below and plots of the data are presented in FIG. 5, wherein the upper graph (A) shows C-PEth16:0/18:1 (μmol/L) on the y-axis versus C-PC16:0/18:1 (μmol/L) on the x-axis, and the lower graph (B) shows PEth/PC on the y-axis versus C-PC16:0/18:1 (μmol/L) on the x-axis.

Coefficients "k", "m" and R-squared for C-PEth16:0/18:1 versus C-PC16:0/18:1 (graph A, FIG. 5) was determined to be 0.0052, –1.2131 and 0.3001, respectively.

Coefficients "k", "m" and R-squared for PEth/PC versus C-PC16:0/18:1 (graph B, FIG. 5) was determined to be 0.000006, –0.0003 and 0.1147, respectively.

| Sample ID | C-PEth16:0/18:1 (μmol/L) | PEth/PC | C-PC16:0/18:1 (μmol/L) |
|---|---|---|---|
| 1 | 0.0875 | 0.000237127 | 369 |
| 2 | 0.118 | 0.000398649 | 296 |
| 3 | 0.168 | 0.000358974 | 468 |
| 4 | 0.0883 | 0.00022075 | 400 |
| 5 | 0.106 | 0.00030814 | 344 |
| 6 | 0.164 | 0.000548495 | 299 |
| 7 | 0.146 | 0.000470968 | 310 |
| 8 | 0.164 | 0.000518987 | 316 |
| 9 | 0.0939 | 0.000287156 | 327 |
| 10 | 0.0724 | 0.000178325 | 406 |
| 11 | 0.311 | 0.001054237 | 295 |
| 12 | 0.233 | 0.000337681 | 690 |
| 13 | 0.283 | 0.0008017 | 353 |
| 14 | 0.271 | 0.000434295 | 624 |
| 15 | 0.214 | 0.000701639 | 305 |
| 16 | 0.371 | 0.000772917 | 480 |
| 17 | 0.224 | 0.000495575 | 452 |
| 18 | 0.274 | 0.00070801 | 387 |
| 19 | 0.292 | 0.000713936 | 409 |
| 20 | 0.201 | 0.000537433 | 374 |
| 21 | 0.774 | 0.001723831 | 449 |
| 22 | 0.829 | 0.001790497 | 463 |
| 23 | 0.701 | 0.001276867 | 549 |
| 24 | 0.731 | 0.001329091 | 550 |
| 25 | 0.63 | 0.000982839 | 641 |

-continued

| Sample ID | C-PEth16:0/18:1 (μmol/L) | PEth/PC | C-PC16:0/18:1 (μmol/L) |
|---|---|---|---|
| 26 | 0.676 | 0.002201954 | 307 |
| 27 | 0.57 | 0.001469072 | 388 |
| 28 | 0.584 | 0.00164507 | 355 |
| 29 | 0.721 | 0.002783784 | 259 |
| 30 | 0.662 | 0.001794038 | 369 |
| 31 | 1.33 | 0.002453875 | 542 |
| 32 | 1.52 | 0.003790524 | 401 |
| 33 | 1.17 | 0.003362069 | 348 |
| 34 | 1.66 | 0.00318618 | 521 |
| 35 | 1.72 | 0.004 | 430 |
| 36 | 1.16 | 0.002672811 | 434 |
| 37 | 1.06 | 0.002476636 | 428 |
| 38 | 1.69 | 0.002816667 | 600 |
| 39 | 0.8 | 0.002179837 | 367 |
| 40 | 0.877 | 0.002260309 | 388 |
| 41 | 3.31 | 0.007133621 | 464 |
| 42 | 2.88 | 0.006385809 | 451 |
| 43 | 2.34 | 0.003738019 | 626 |
| 44 | 2.32 | 0.004377358 | 530 |
| 45 | 4.48 | 0.005524044 | 811 |
| 46 | 2.27 | 0.006069519 | 374 |
| 47 | 4.28 | 0.00827853 | 517 |
| 48 | 3.32 | 0.005684932 | 584 |
| 49 | 2.93 | 0.004283626 | 684 |
| 50 | 2.7 | 0.005684211 | 475 |

Example 2

A dataset consisting of the concentration of PEth 16:0/20:4 (C-PEth16:0/20:4), the concentration of the corresponding phosphatidyl choline bio-precursor (C-PC16:0/20:4), and the ratio (PEth/PC) between the concentration of PEth 16:0/20:4 and the concentration of the corresponding phosphatidyl choline bio-precursor, was collected by the analysis of the 50 samples as described above. The specific values of the dataset are depicted in the table below and plots of the data are presented in FIG. 6, wherein the upper graph (A) shows C-PEth16:0/20:4 (μmol/L) on the y-axis versus C-PC16:0/20:4 (μmol/L) on the x-axis, and the lower graph (B) shows PEth/PC on the y-axis versus C-PC16:0/20:4 (μmol/L) on the x-axis.

Coefficients "k", "m" and R-squared for C-PEth16:0/20:4 versus C-PC16:0/20:4 (graph A, FIG. 6) was determined to be 0.0026, −0.2204 and 0.1312, respectively.

Coefficients "k", "m" and R-squared for PEth/PC versus C-PC16:0/20:4 (graph B, FIG. 6) was determined to be 0.000007, −0.00003 and 0.043, respectively.

| Sample ID | C-PEth16:0/20:4 (μmol/L) | PEth/PC | C-PC16:0/20:4 (μmol/L) |
|---|---|---|---|
| 1 | 0.0205 | 0.000112022 | 183 |
| 2 | 0.0261 | 0.00023945 | 109 |
| 3 | 0.0216 | 0.000124138 | 174 |
| 4 | 0.0132 | 8.30189E−05 | 159 |
| 5 | 0.0183 | 6.82836E−05 | 268 |
| 6 | 0.0384 | 0.000216949 | 177 |
| 7 | 0.0305 | 0.000173295 | 176 |
| 8 | 0.0445 | 0.000241848 | 184 |
| 9 | 0.0142 | 9.93007E−05 | 143 |
| 10 | 0.0125 | 6.86813E−05 | 182 |
| 11 | 0.0329 | 0.000209554 | 157 |
| 12 | 0.0376 | 0.000179904 | 209 |
| 13 | 0.0792 | 0.000375355 | 211 |
| 14 | 0.0889 | 0.000402262 | 221 |
| 15 | 0.0538 | 0.000407576 | 132 |
| 16 | 0.0763 | 0.000556934 | 137 |
| 17 | 0.0582 | 0.000330682 | 176 |
| 18 | 0.0824 | 0.000597101 | 138 |
| 19 | 0.0708 | 0.0004425 | 160 |
| 20 | 0.0338 | 0.000307273 | 110 |
| 21 | 0.168 | 0.000884211 | 190 |
| 22 | 0.198 | 0.000965854 | 205 |
| 23 | 0.0954 | 0.000437615 | 218 |
| 24 | 0.07 | 0.000673077 | 104 |
| 25 | 0.139 | 0.00065566 | 212 |
| 26 | 0.173 | 0.001130719 | 153 |
| 27 | 0.205 | 0.000990338 | 207 |
| 28 | 0.16 | 0.001151079 | 139 |
| 29 | 0.125 | 0.001709986 | 73.1 |
| 30 | 0.161 | 0.000879781 | 183 |
| 31 | 0.275 | 0.001165254 | 236 |
| 32 | 0.5 | 0.002380952 | 210 |
| 33 | 0.28 | 0.001656805 | 169 |
| 34 | 0.273 | 0.001467742 | 186 |
| 35 | 0.2 | 0.00106383 | 188 |
| 36 | 0.0762 | 0.000482278 | 158 |
| 37 | 0.441 | 0.00175 | 252 |
| 38 | 0.417 | 0.001985714 | 210 |
| 39 | 0.115 | 0.00072327 | 159 |
| 40 | 0.145 | 0.00090625 | 160 |
| 41 | 0.836 | 0.004331606 | 193 |
| 42 | 0.355 | 0.002909836 | 122 |
| 43 | 0.443 | 0.002295337 | 193 |
| 44 | 0.737 | 0.002924603 | 252 |
| 45 | 0.952 | 0.004051064 | 235 |
| 46 | 0.206 | 0.001089947 | 189 |
| 47 | 1.01 | 0.00510101 | 198 |
| 48 | 0.74 | 0.00352381 | 210 |
| 49 | 1.12 | 0.006120219 | 183 |
| 50 | 0.498 | 0.002946746 | 169 |

Example 3

A dataset consisting of the concentration of PEth 18:1/18:1 (C-PEth18:1/18:1), the concentration of the corresponding phosphatidyl choline bio-precursor (C-PC18:1/18:1), and the ratio (PEth/PC) between the concentration of PEth 18:1/18:1 and the concentration of the corresponding phosphatidyl choline bio-precursor, was collected by the analysis of the 50 samples as described above. The specific values of the dataset are depicted in the table below and plots of the data are presented in FIG. 7, wherein the upper graph (A) shows C-PEth18:1/18:1 (μmol/L) on the y-axis versus C-PC18:1/18:1 (μmol/L) on the x-axis, and the lower graph (B) shows PEth/PC on the y-axis versus C-PC18:1/18:1 (μmol/L) on the x-axis.

Coefficients "k", "m" and R-squared for C-PEth18:1/18:1 versus C-PC18:1/18:1 (graph A, FIG. 7) was determined to be 0.006, −0.0771 and 0.2238, respectively.

Coefficients "k", "m" and R-squared for PEth/PC versus C-PC18:1/18:1 (graph B, FIG. 6) was determined to be 0.00008, −0.0008 and 0.0669, respectively.

| Sample ID | C-PEth18:1/18:1 (μmol/L) | PEth/PC | C-PC18:1/18:1 (μmol/L) |
|---|---|---|---|
| 1 | 0.0282 | 0.001205128 | 23.4 |
| 2 | 0.033 | 0.001182796 | 27.9 |
| 3 | 0.0293 | 0.000885196 | 33.1 |
| 4 | 0.0185 | 0.000612583 | 30.2 |
| 5 | 0.0193 | 0.000540616 | 35.7 |
| 6 | 0.0242 | 0.001095023 | 22.1 |
| 7 | 0.025 | 0.000822368 | 30.4 |
| 8 | 0.0242 | 0.001157895 | 20.9 |
| 9 | 0.0206 | 0.000895652 | 23 |

-continued

| Sample ID | C-PEth18:1/18:1 (µmol/L) | PEth/PC | C-PC18:1/18:1 (µmol/L) |
|---|---|---|---|
| 10 | 0.0139 | 0.000695 | 20 |
| 11 | 0.0329 | 0.001321285 | 24.9 |
| 12 | 0.0299 | 0.000808108 | 37 |
| 13 | 0.0408 | 0.001291139 | 31.6 |
| 14 | 0.0441 | 0.001072993 | 41.1 |
| 15 | 0.03 | 0.0012 | 25 |
| 16 | 0.0705 | 0.001241197 | 56.8 |
| 17 | 0.0348 | 0.001137255 | 30.6 |
| 18 | 0.0354 | 0.001372093 | 25.8 |
| 19 | 0.0391 | 0.001120344 | 34.9 |
| 20 | 0.0369 | 0.000770355 | 47.9 |
| 21 | 0.0848 | 0.002585366 | 32.8 |
| 22 | 0.095 | 0.002429668 | 39.1 |
| 23 | 0.0747 | 0.001895939 | 39.4 |
| 24 | 0.104 | 0.001538462 | 67.6 |
| 25 | 0.0796 | 0.001621181 | 49.1 |
| 26 | 0.06 | 0.002390438 | 25.1 |
| 27 | 0.0766 | 0.002678322 | 28.6 |
| 28 | 0.0637 | 0.002548 | 25 |
| 29 | 0.114 | 0.003247863 | 35.1 |
| 30 | 0.0806 | 0.003041509 | 26.5 |
| 31 | 0.144 | 0.0045 | 32 |
| 32 | 0.185 | 0.005709877 | 32.4 |
| 33 | 0.118 | 0.00291358 | 40.5 |
| 34 | 0.307 | 0.004865293 | 63.1 |
| 35 | 0.173 | 0.006290909 | 27.5 |
| 36 | 0.0926 | 0.002550964 | 36.3 |
| 37 | 0.129 | 0.004607143 | 28 |
| 38 | 0.199 | 0.004364035 | 45.6 |
| 39 | 0.0715 | 0.00232899 | 30.7 |
| 40 | 0.0936 | 0.002971429 | 31.5 |
| 41 | 0.455 | 0.010731132 | 42.4 |
| 42 | 0.402 | 0.009262673 | 43.4 |
| 43 | 0.282 | 0.004227886 | 66.7 |
| 44 | 0.321 | 0.00737931 | 43.5 |
| 45 | 0.438 | 0.010045872 | 43.6 |
| 46 | 0.232 | 0.009430894 | 24.6 |
| 47 | 0.571 | 0.01510582 | 37.8 |
| 48 | 0.396 | 0.008081633 | 49 |
| 49 | 0.457 | 0.008805395 | 51.9 |
| 50 | 0.365 | 0.009240506 | 39.5 |

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method for assessment of previous ethanol exposure in a subject comprising the steps of:
   (i) obtaining a sample from the body of the subject;
   (ii) removing one or both of the carboxylic acid residues from compounds of Formula II present in said sample by selective hydrolysis,

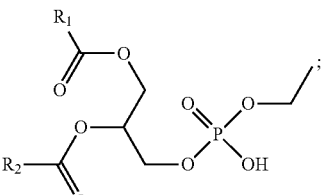

(II)

(iii) quantitatively determining a level of reaction product from step (ii); and
   (iv) using said level to assess previous ethanol exposure in the subject;
   wherein
   the subject is a human or animal;
   said selective hydrolysis is performed by a hydrolase selected from the group consisting of pancreatic triacylglycerol lipases, lipoprotein lipases, lingual lipase, monoacylglycerol lipases, diacylglycerol lipases, hepatic lipases, triglyceride lipases; and
   $R_1$ and $R_2$ are independently selected from straight or branched $C_{9-39}$ alkyl, $C_{9-39}$ alkenyl, $C_{9-39}$ alkdienyl and $C_{9-39}$ alktrienyl.

2. The method according to claim 1, further comprising the steps of removing carboxylic acid residues covalently bound as esters in one or several bio-precursors of phosphatidylethanol (PEth) present in said sample by selective hydrolysis to yield corresponding alcohol or alcohols;
   quantitatively determining a level of said corresponding alcohol or alcohols;
   obtaining a ratio between said level of said corresponding alcohol or alcohols and said level
   using said ratio between said level of said corresponding alcohol or alcohols and said level of said reaction product from step (ii) in claim 1 to assess previous ethanol exposure in the subject.

3. The method according to claim 2, wherein said bio-precursors of PEth are selected from the group consisting of phosphatidyl serine, phosphatidyl ethanolamine, phosphatidyl inositol, cardiolipin and phosphatidyl choline.

4. A method for assessment of previous absolute ethanol consumption in a subject comprising the steps of:
   (i) obtaining a first measure of previous ethanol exposure in the subject according to claim 1, said first measure being the level of said reaction product from step (ii);
   (ii) obtaining a second measure of previous ethanol exposure in at least one reference according to claim 1, said second measure being said level of the reaction product from step (ii); and
   (iii) comparing said first measure with said second measure to determine the previous absolute ethanol consumption in the subject;
   wherein
   said first measure is obtained by a method which is the same as the method by which said second measure is obtained; and
   the at least one reference is a human or animal which has been exposed to a known amount of ethanol prior to obtaining a sample used for obtaining said second measure.

5. A method for assessment of previous ethanol exposure in a subject comprising the steps of:
  (i) obtaining a sample from the body of the subject;
  (ii) removing carboxylic acid residues of compounds of Formula II present in said sample to yield a compound of Formula IIc by selective transesterification

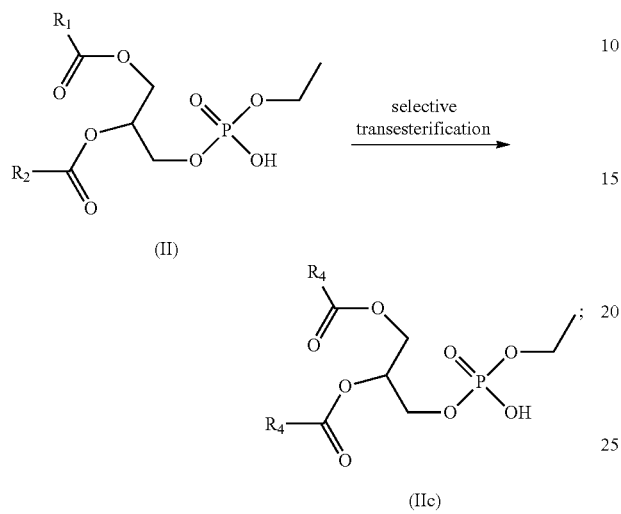

(iii) quantitatively determining a level of said compound of Formula IIc; and
  (iv) using said level of said compound of Formula IIc to assess previous ethanol exposure in the subject;
  wherein
  the subject is a human or animal;
  $R_1$ and $R_2$ are independently selected from straight or branched $C_{9-39}$ alkyl, $C_{9-39}$ alkenyl, $C_{9-39}$ alkdienyl and $C_{9-39}$ alktrienyl; and
  $R_4$ is a saturated or unsaturated straight carbon chain, or a carboxylic acid residue of a synthetically produced carboxylic acid.

6. The method according to claim 5, wherein at least one of R1 and R2 is different from R4.

7. The method according to claim 5, further comprising the steps of
  exchanging the carboxylic acid residues covalently bound as esters in one or several bio-precursors of PEth present in said sample by selective transesterification to yield corresponding transesterified ester or esters;
  quantitatively determining a level of said corresponding transesterified ester or esters;
  obtaining a ratio between said level of said corresponding transesterified ester or esters and said level of compound of Formula IIc; and
  using said ration between said level of said corresponding transesterified ester or esters and said level of compound of Formula IIc to assess previous ethanol exposure in the subject.

8. The method according to claim 7, wherein said bio-precursors of PEth are selected from the group consisting of phosphatidyl serine, phosphatidyl ethanolamine, phosphatidyl inositol, cardiolipin and phosphatidyl choline.

9. The method according to claim 5, further comprising the steps of
  removing carboxylic acid residues from compounds of Formula I present in said sample to yield a compound of Formula Ic by selective transesterification;

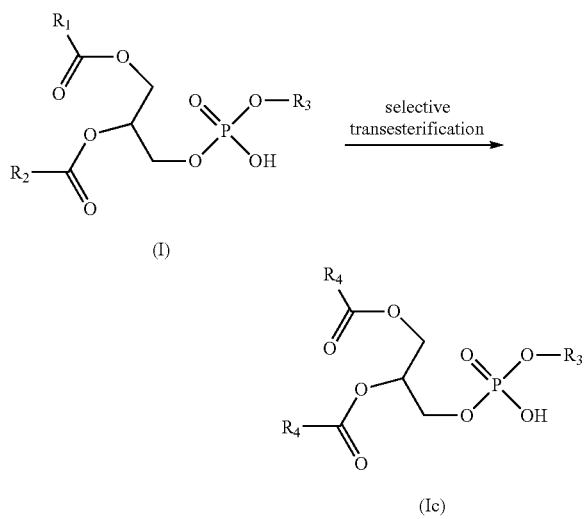

quantitatively determining the level of said compound of Formula Ic;
  obtaining a ratio between the level of said compound of Formula Ic and said compound of Formula IIc; and
  using said ratio between the level of said compound of Formula Ic and said compound of Formula IIc to assess previous ethanol exposure in the subject;
  wherein
  said compound of Formula I is a bio-precursors of PEth;
  $R_1$ and $R_2$ are independently selected from straight or branched $C_{9-39}$ alkyl, $C_{9-39}$ alkenyl, $C_{9-39}$ alkdienyl and $C_{9-39}$ alktrienyl;
  R4 is a saturated or unsaturated straight carbon chain, or the carboxylic acid residue of a synthetically produced carboxylic acid; and
  $R_3$ is selected from

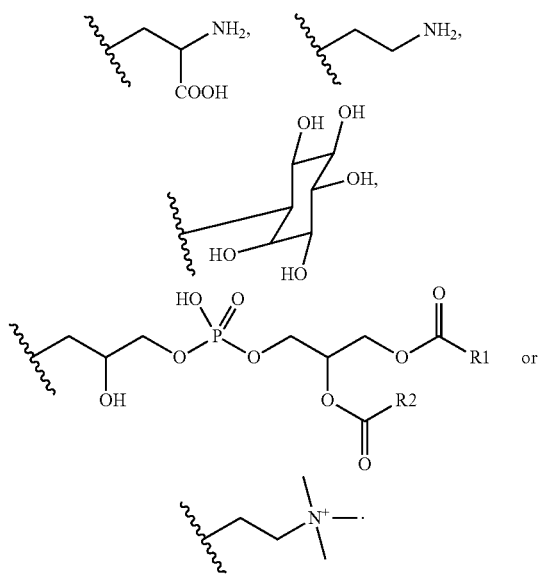

10. The method according to claim 9, wherein at least one of R1 and R2 is different from R4.

11. The method according to claim 9, wherein all substituents R4 of compounds of Formula Ic are the same as all substituents R4 of compounds of Formula IIc.

12. A method according to claim 9, wherein R4 of compounds of formula Ic or IIc comprise one or several UV-absorbing groups selected from 6- or 5-membered aromatic rings or condensed aromatic systems.

13. A method according to claim 5, wherein R4 of compounds of formula Ic or IIc comprise one or several UV-absorbing groups selected from 6- or 5-membered aromatic rings or condensed aromatic systems.

14. A method for assessment of previous absolute ethanol consumption in a subject comprising the steps of:
   (i) obtaining a first measure of previous ethanol exposure in the subject according to claim 5 said first measure being said level of said compound of Formula IIc;
   (ii) obtaining a second measure of previous ethanol exposure in at least one reference according to claim 5, said second measure being said level of said compound of Formula IIc; and
   (iii) comparing said first measure with said second measure to determine the previous absolute ethanol consumption in the subject;
   wherein
   said first measure is obtained by a method which is the same as the method by which said second measure is obtained; and
   the at least one reference is a human or animal which has been exposed to a known amount of ethanol prior to obtaining a sample used for obtaining said second measure.

15. A method for assessment of previous ethanol exposure in a subject comprising the steps of:
   (i) obtaining a sample from the body of the subject;
   (ii) quantitatively determining a level of one or several bio-precursors of PEth and a level of corresponding one or several PEth-homologues in said sample;
   (iii) obtaining a ratio between said level of one or several bio-precursors of PEth and said level of corresponding one or several PEth-homologues; and
   (iv) using said ratio between said level of one or several bio-precursors of PEth and said level of the corresponding one or several PEth-homologues to assess previous ethanol exposure in the subject;
   wherein
   the subject is a human or animal.

16. The method according to claim 15, wherein said one or several PEth-homologues are independently selected from the group consisting of PEth 16:0/18:1, PEth 16:0/18:2, PEth 16:0/20:4, PEth 18:0/18:1, PEth 18:1/18:1 and PEth 18:0/18:2, or any one of the corresponding regioisomers in which the carboxylic acid residues have switched places on the glycerol backbone.

17. The method according to claim 15, wherein said one or several bio-precursors of PEth are independently selected from the group consisting of phosphatidyl serine, phosphatidyl ethanolamine, phosphatidyl inositol, cardiolipin and phosphatidyl choline.

18. The method according to claim 15, wherein said ratio is
   a ratio between the sum of concentrations or the sum of amounts of at least two bio-precursors of PEth in said sample and the sum of concentrations or the sum of amounts, respectively, of at least two PEth-homologues in the same sample; or
   a ratio between the sum of concentrations or the sum of amounts of at least two PEth-homologues in said sample and the sum of concentrations or the sum of amounts, respectively, of at least two bio-precursors of PEth in the same sample;
   each one of said at least two PEth-homologues being a compound formed in-vivo from one of said at least two bio-precursors of PEth in the presence of ethanol.

19. A method for assessment of previous absolute ethanol consumption in a subject comprising the steps of:
   (i) obtaining a first measure of previous ethanol exposure in the subject according to claim 15, said first measure being said ratio obtained in step (iii) of claim 15;
   (ii) obtaining a second measure of previous ethanol exposure in at least one reference according to claim 15, said second measure being said ratio obtained in step (iii) of claim 15; and
   (iii) comparing said first measure with said second measure to determine the previous absolute ethanol consumption in the subject;
   wherein
   said first measure is obtained by a method which is the same as the method by which said second measure is obtained; and
   the at least one reference is a human or animal which has been exposed to a known amount of ethanol prior to obtaining a sample used for obtaining said second measure.

20. A method for assessment of previous ethanol exposure in a subject comprising the steps of:
   (i) obtaining a sample from the body of the subject;
   (ii) quantitatively determining a level of one or several bio-precursors of ethyl-sphingomyelin and a level of corresponding one or several ethyl-sphingomyelin homologues in said sample;
   (iii) obtaining a ratio between said level of one or several bio-precursors of ethyl-sphingomyelin and said level of the corresponding one or several ethyl-sphingomyelin homologues; and
   (iv) using said ratio between said level of one or several bio-precursors of ethyl-sphingomyelin and said level of the corresponding one or several ethyl-sphingomyelin homologues to assess previous ethanol exposure in the subject;
   wherein
   the subject is a human or animal.

21. A method for assessment of previous ethanol exposure in a subject comprising the steps of:
   (i) obtaining a blood sample of the subject;
   (ii) quantitatively determining a level of one or several PEth-homologues, or a level of one or several ethyl-sphingomyelin homologues, in said blood sample, and determining a level of a measurable parameter representing an amount of cellular material in said blood sample;
   (iii) obtaining a ratio between said level of one or several PEth-homologues or said level of one or several ethyl-sphingomyelin homologues, and said level of said measurable parameter; and
   (iv) using said ratio between said level of one or several PEth-homologues or one or several ethyl-sphingomyelin homologues, and said level of said measurable parameter to assess previous ethanol exposure in the subject;
   wherein
   the subject is a human being or animal; and
   said measurable parameter is haemoglobin or the erythrocyte volume fraction.

22. A method for assessment of the history of previous ethanol exposure in a subject comprising the steps of:
  (i) obtaining a sample from the body of the subject;
  (ii) quantitatively determining a level of one or several bio-precursors of PEth, or a level of one or several bio-precursors of ethyl-sphingomyelin, and a level of corresponding one or several first bio-markers of ethanol being PEth or a level of one or several ethyl-sphingomyelin homologues, respectively, and quantitatively determining a level of a second bio-marker of ethanol;
  (iii) comparing said level of one or several bio-precursors of PEth or said level of one or several bio-precursors of ethyl-sphingomyelin, said level of the corresponding one or several first bio-markers of ethanol, and said level of said second bio-marker of ethanol to determine the history of previous absolute ethanol consumption in the subject;
  wherein
  the subject is a human or animal.

* * * * *